United States Patent [19]

Mutschler et al.

[11] Patent Number: 5,661,181

[45] Date of Patent: Aug. 26, 1997

[54] NON-CYCLIC ESTERS FOR PEST CONTROL

[75] Inventors: Martha A. Mutschler; Bruce Ganem, both of Ithaca, N.Y.

[73] Assignee: Cornell Research Foundation, Inc., Ithca, N.Y.

[21] Appl. No.: 390,409

[22] Filed: Feb. 16, 1995

[51] Int. Cl.⁶ .................................................. A01N 37/02

[52] U.S. Cl. ........................... 514/552; 514/546; 514/547

[58] Field of Search ..................................... 514/547, 546, 514/552

[56] References Cited

U.S. PATENT DOCUMENTS 3,615,454  10/1971  Crescon et al. ..................... 96/35.1

*Primary Examiner*—Brian M. Burn
*Attorney, Agent, or Firm*—Bruce F. Jacobs; Diderico Van Eyl

[57] ABSTRACT

A method for repelling insects from plants with non-cyclic esters is disclosed. The esters are prepared from a non-cyclic polyhydroxyl compound having from about 3 to about 5 carbon atoms and at least three hydroxyl groups and a carboxylic acid. In the esters at least two of the hydroxyl groups are esterified and the total number of carbon atoms in all of the ester groups is from about 9 to about 19.

22 Claims, No Drawings

NON-CYCLIC ESTERS FOR PEST CONTROL

BACKGROUND OF THE INVENTION

Insects frequently damage plants and prevent them from being used for desirable and beneficial purposes. The tomato fruitworm, *Helicoverpa zea* (Boddie), and the beet armyworm, *Spodoptera exigua* (Hubner), for instance, are two of the most serious insect pests of fresh-market and processing tomatoes. Neonates of both species feed on foliage for several days before migrating to the tomato fruit. Larvae bore into fruit, providing entry for the decay organisms, and each larva can damage several fruit before pupation (Wilcox et. al. 1956, University of California, 1985). In California, about 30 million dollars is lost annually from damage to processing tomatoes by larvae of *H. zea* and *S. exigua* (Johnson et al. 1986). Because the damage insects cause plants results in such high losses, there is a need for effective strategies to manage pests.

U.S. Pat. No. 4,943,563 teaches the use of cyclic 2,3,4-triacylhexoses to repel insects from plants. The cyclic hexose esters may be formulated into insect repellant compositions by blending them with inert carriers and then used by depositing the resulting compositions upon a surface to be protected from attack by the insects. The cyclic 2,3,4-triacyl hexoses may be utilized as either individual compounds or in mixtures derived, for example, as the result of selective extraction and purification of the epicuticular exudate from plant parts of the plant species *Lycopersicon pennellii*, its hybrids and progeny.

In the continuing search for more effective pest control agents, it has now been discovered that certain specific non-cyclic esters are effective in preventing insect damage to plants, such as tomatoes and plants of the *Lycopersicon pennellii* species.

The non-cyclic esters are known compounds having been used previously for high speed engine lubricants and synthetic fibers.

SUMMARY OF THE INVENTION

The present invention is directed to an insect repellent compound having the general formula:

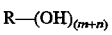

wherein R is a non-cyclic straight chain or branched hydrocarbon group having from about 3 to about 5 carbon atoms, $R^1$ is an alkyl group having from about 1 to about 18 carbon atoms, m is an integer from about 0 to about 5, n is an integer of at least 2 and up to about 6, m+n is an integer of at least 3, and the total number of carbon atoms in the $R^1$ groups is about 9 to about 19.

The invention further provides a method of protecting a plant from attack by insects by applying to said plant the insect-repellent compound in an amount which is sufficient to trap or capture an adult insect but which amount is sufficient to cause the insect to not damage the plant by feeding thereon.

DETAILED DESCRIPTION OF THE INVENTION

The insect repellent esters forming the basis for the present invention have the general formula:

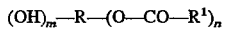

wherein R is a non-cyclic straight chain or branched hydrocarbon group having from about 3 to about 5 carbon atoms, $R^1$ is an alkyl group having from about 1 to about 18 carbon atoms, m is an integer from about 0 to about 5, n is an integer of at least 2 and up to about 6, m+n is an integer of at least 3, and the total number of carbon atoms in the $R^1$ groups is from about 9 to about 19.

The esters are prepared by reaction of a suitable polyol with one or more carboxylic acids. Specifically, R is derived from a polyol of the general formula:

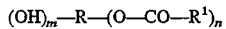

wherein m+n is three or greater. Suitable R groups are non-cyclic hydrocarbons, either straight chain or branched. While R is preferably unsubstituted beyond the hydroxyl groups, it may contain substituents. Such substituents include alcohol $C_{1-4}$, alkoxy $C_{1-4}$, cyano and halo. Preferred such substituents are —$CH_2OH$, —CN, —$OCH_3$ and —F. Glycerol and pentaerythritol are presently the preferred polyols.

Although each $R^1$ is preferably an unsubstituted straight chain or branched hydrocarbon group, $R^1$ may contain substituents. Such substituents include alkoxy, carboxyalkyl $C_{1-4}$, hydroxyalkyl $C_{1-4}$, and halo. Preferred such substituents are —OH, —$OCH_3$, —$OCOCH_3$, $CH_2OH$, and F.

Specific compounds within the scope of the present invention include: tributyrin, dicaprylin, dicaproin, pentaerythrityl tributyrate, pentaerythrityl tetrabutyrate, pentaerythrityl dihexanoate, pentaerythrityltrihexanoate, pentaerythritylmonobutyratetripropionate, pentaerythrityl dibutyratedipropionate, pentaerythrityl dibutyratemonopropionate, pentaerythrityl monobutyratedipropionate, pentaerythrityl tributyratemonopropionate, pentaerythrityl monobutyratetrihexanoate, pentaerythrityldibutyratemonohexanoate, pentaerythrityl dibutyradihexanoate, pentaerythrityl tributyratemonohexanoate, meso or D L-erythritol dibutyrate (1,2;1,3;1,4;2,3 isomers); meso or D L-erythritol tributyrate (1,2,3; 1,2,4 isomers); meso or D or L-erythritol dihexanoate (1,2;1,3;1,4;2,3 isomers); meso or D or L-erythritol trihexanoate (1,2,3;1,2,4 isomers).

More specifically, the esters may be prepared by a conventional esterification reaction between a polyol and one or more carboxylic acids. The reaction occurs under conventional experimental conditions well known in the art, such as the reaction of an appropriate quantity of acid halide, imidazolide, or anhydride with a polyol dissolved in pyridine or triethylamine at about 0° C., or room temperature from about three to about twelve hours.

The non-cyclic esters of the invention repel insects from plant surfaces they coat, and are particularly suitable for preventing damage to plants by plant-eating insects. In addition, the esters prevent the insects from ovipositing on the plant surfaces. Examples of insects which may be repelled by the esters of this invention include those of the orders: Acarina, Coleoptera, Diptera, Homoptera, Lepidoptera, Thysandoptera, and the like. Thus, insects which are protected against those belonging to families including Agromyzidae, Aleyrodidae, Aphididae, Chrysomelidae, Cicadellidae, Gelechiidae, Meloidae, Noctuidae, Pseudococcidae, Aphingidae, Tarsonmidae, Tetranychidae, and Thripidae. In particular, the esters of this invention provide protection from specific insects such as: tarsonemid mites, carmine spider mites, two spotted spider mites, leaf beetles, blister beetles, potato flea beetles, tomato flea beetles, flea beetles, tobacco flea beetles, leafminer flies, cowpea aphids, bean aphids, melon aphids, buckthorn aphids, foxglove aphids, aphids, potato leafhoppers, potato aphids, aster leafhoppers, green peach aphids, citrus mealey bugs, silverleaf whiteflies, American bollworms, cotton budworms, cotton bollworms, tomato pinworms, tobacco hornworms, variegated cutworms, potato tubermoths, beet armyworms, fall armyworms, thrips, onion thrips, and the like.

The plants which are protected from such insects are those which, in the absence of the non-cyclic esters of this invention, would otherwise be damaged or killed by insects. Such plants include both ornamental plants and productive plants. Examples of ornamental plants include: roses, chrysanthemums, carnations, poinsettias, impatiens, and a wide range of other trees, shrubs, and herbacaous annuals. Examples of productive plants include: corn, soybean, sunflower, tomato, tobacco, potato, wheat, oats, alfalfa, and other crop plants. In general, because the host range of insects which are repelled by the esters of this invention is extremely broad, the range of plants which are protected thereby is equally as broad. In addition, insects have been found to not oviposit on treated plants.

The insect-repelling esters of this invention may be used either alone, in mixtures, or more preferably with inert carriers customarily employed in conventional formulation practice, and thus may be processed in known manners. For example, these esters may be processed into the form of emulsion concentrates, directly sprayable or dilutable solutions, diluted emulsions, diluted emulsions, wettable powders, dusts or granules, and also encapsulations or microencapsulation in, for example, polymeric substances. The processes used to apply these esters, such as by spraying, atomizing, dusting, scattering or pouring and likewise the specific form of composition, are selected based upon the objectives to be achieved and the given conditions.

The insect repellent compositions, i.e. the compositions or preparations containing the insect-repelling esters, and preferably a solid or liquid carrier additive, are produced by a known manner. For example, intimate mixing and/or grinding of the active ingredients with extenders, such as with solvents, solid carriers, and optionally surface-active compounds may produce a suitable insect-repellent composition.

Suitable solvents include: aromatic hydrocarbons, preferably the fraction of $C_8$ to $C_{12}$, such as xylene mixtures or substituted naphthalenes, aliphatic hydrocarbons, such as cyclohexanes or paraffins, alcohols and glycols, as well as ethers thereof, such as ethanol, ethylene glycol, ethylene glycol monomethyl or ethyl ethers, ketones such as cyclohexane, strongly polar solvents, such as N-methyl-2-pyrrolidone, dimethyl sulfoxide or dimethylformamide, as well as optionally expoxidized vegetable oils, such as epoxidized coconut oil or soybean oil, or water.

The solid carriers used, i.e. dusts and dispersible powders, are as a rule natural mineral fillers, such as calcite, talcum, kaolin, montmorillonite or attapulgite. In order to improve the physical properties of an insect-repelling composition, highly dispersed silicic acid or highly dispersed absorbent polymers may also be added. Suitable granulated absorptive carriers are porous and include materials such as pumice, ground brick, sepiolite or bentonite. Suitable nonsorbent carriers include materials such as calcite or sand. A great number of pregranulated materials of inorganic or organic nature, such as in particular dolomite or ground plant residues may also be used.

Depending on the active ingredients to be formulated, suitable surface-active compounds are: nonionic, cationic and/or anionic compounds having good emulsifying, dispersing and wetting properties.

The insect-repellant compositions will generally contain about 0.01 to about 99.99% percent by weight of one or more suitable esters with the balance being a solid or liquid carrier to assist in the delivery of the active ingredient onto the plant surfaces to be protected.

Whereas commercial products are preferably in the form of concentrated compositions, the preparations employed by the end-user will have, as a rule, a considerably lower concentration of active ingredient.

The compositions can also contain further additives, such as stabilizers, antifoaming agents, viscosity regulators, binders, and adhesives, as well as fertilizers or other active ingredients for obtaining desired effects.

| FORMULATION EXAMPLES OF LIQUID ACTIVE INGREDIENTS (% = PERCENT BY WEIGHT) | | | |
|---|---|---|---|
| 1. Emulsion concentrates | (a) | (b) | (c) |
| active ingredient | 25% | 40% | 50% |
| calcium dodecyl benzenesulfonate | 5% | 8% | 6% |
| castor oil-polyethylene glycol ether (36 mols of ethylene oxide) | 5% | — | — |
| tributylphenol-polyethylene glycol ether (30 mols of ethylene oxide) | — | 12% | 4% |
| cyclohexanone | — | 15% | 20% |
| xylene mixture | 65% | 25% | 20% |

Emulsions of the required concentrations can be produced from these concentrates by dilution with methanol.

| 2. Granules | (a) | (b) |
|---|---|---|
| active ingredient | 5% | 10% |
| kaolin | 94% | — |
| highly dispersed silicic acid | 1% | — |
| attapulgite | — | 90% |

The active ingredient is dissolved in 2-propanol, the solution is sprayed onto the carrier, and the solvent is then evaporated off in vacuo.

| 3. Dusts | (a) | (b) |
|---|---|---|
| active ingredient | 2% | 5% |
| highly dispersed silicic acid | 1% | 5% |
| talcum | 97% | — |
| kaolin | — | 90% |

Dusts ready for use are obtained by the intimate mixture together of the carriers with the active ingredient.

| FORMULATION EXAMPLES OF LIQUID ACTIVE INGREDIENTS (% = PERCENT BY WEIGHT) | | | |
|---|---|---|---|
| 4. Wettable Powders | (a) | (b) | (c) |
| active ingredient | 25% | 50% | 75% |
| sodium lignin sulfonate | 5% | 5% | — |
| sodium lauryl sulfate | 3% | — | 5% |
| sodium diisobutylnapthalene sulfonate | — | 6% | 10% |
| octylphenolpolyethylene glycol ether (7–8 mols of ethylene oxide) | — | 2% | — |
| highly dispersed silicic acid | 5% | 10% | 10% |
| kaolin | 62% | 27% | — |

The active ingredient is well mixed with additives and the mixture is thoroughly ground in a suitable mill. The wettable powders which are obtained may be diluted with water to give suspensions of the required concentrations.

| 5. Emulsion concentrate | |
|---|---|
| active ingredient | 10% |
| octylphenol polyethylene glycol ether (4–5 mols of ethylene oxide) | 6% |
| castor oil polyglycol ether (36 mols of ethylene oxide) | 4% |
| cyclohexanone | 30% |
| xylene mixtures | 50% |

Emulsions of the concentrate required can be obtained from this concentrate by dilution with water.

| 6. Dusts | (a) | (b) |
|---|---|---|
| active ingredients | 5% | 8% |
| talcum | 95% | — |
| kaolin | — | 92% |

Dusts ready for use are obtained by mixing the active ingredient with the carriers, and grinding the mixture in a suitable mill.

| 7. Extruded Granulate | |
|---|---|
| active ingredient | 10% |
| sodium lignin sulfonate | 2% |
| carboxymethyl cellulose | 1% |
| kaolin | 87% |

The active ingredient is mixed and ground with the additives, and the mixture is moistened with water. This mixture is extruded, granulated and then dried in a stream of air.

| 8. Coated granulate | |
|---|---|
| active ingredient | 3% |
| polyethylene glycol (M.W. 200) | 3% |
| kaolin | 94% |

The finely ground active ingredient is evenly applied, in a mixer, to the kaolin moistened with polyethylene glycol. Dust-free coated granules are obtained in like manner.

| 9. Suspension concentrate | |
|---|---|
| active ingredient | 40% |
| ethylene glycol | 10% |
| nonylphenolpolyethylene glycol ether (15 mols of ethylene oxide) | 6% |
| sodium lignin sulfonate | 10% |
| carboxymethyl cellulose | 1% |
| 37% aqueous formaldehyde solution | 0.2% |
| silicone oil in the form of a 75% aqueous emulsion | 0.8% |
| water | 32% |

The finely ground active ingredient is intimately mixed with the additives. There is obtained a suspension concentrate from which can be produced, by dilution with water, suspensions of the concentrations required.

The non-cyclic ester insect-repellents will normally be deposited upon the substrate to be protected in an amount of about 10 to about 1000 mmol/cm$^2$ of leaf surface, although specific amounts to be used in specific circumstances will be determined by routine tests of the specific plant to be protected from a specific insect or group of insects which are expected to come in contact with that plant.

Having generally describe the invention, a more complete understanding can be obtained by reference to the following specific examples which are include for illustrative purposes only and are not intended to be limiting unless otherwise specified. All parts and percents are by weight unless otherwise specified.

EXAMPLE 1

In this example, pentaerythritol tributyrate, the tributyl ester of pentaerythritol, was synthesized from pentaerythritol and butyryl chloride as follows. To a solution of pentaerythritol (0.99 g, 7.28mmol) in dry pyridine (50 mL, under argon) at 0° C. was added butyryl chloride (2.3 mL, 22 mmol, 3 equiv) dropwise over one hour. The ice bath was removed after one hour, and the reaction stirred 24 hours at room temperature. Water (7 mL) was added and the bulk of pyridine was removed on the rotary evaporator at 2 Torr. The residue was dissolved in 1N HCL (12 mL) and the pentaerythritol esters extracted with CHCl$_3$ (3×20 mL). The combined organic extracts were dried (MGSO$_4$) and concentrated under vacuum to an oil (2.73 g). Purification by flash column chromatography using silica gel afforded the desired triester pentaerythritol tributyrate (1.34 g; 53%) as well as pentaerythritol dibutyrate (0.51 g; 26%) and pentaerythritol tetrabutyrate (0.42 g; 14%).

EXAMPLE 2

The process of Example 1 was repeated and the following esters were prepared:

a: pentaerythritol dipropionate b: pentaerythritol tripropionate c: pentaerythritol tetrapropionate d: pentaerythritol dihexanoate e: pentaerythritol trihexanote

EXAMPLE 3

In this example, the stoichiometry of Example 1 was modified using pentaerythritol (1.92 g; 14 mmol) and butyryl chloride (0.75 mL; 0.5 equiv) and pyridine (100 mL) to produce pentaerythritol monobutyrate (0.74 g; 47%).

EXAMPLE 4

The process of Example 3 was repeated and the following esters were prepared:

(a) pentaerythritol monopropionate (b) pentaerythritol monohexanoate

EXAMPLE 5

In this example, pentaerythritol dibutyratedipropionate was prepared from pentaerythritol dibutyrate as follows. To a solution of pentaerythritol dibutyrate (0.5 g; 1.81 mmol) in dry pyridine (10 mL, under argon) at 0° C. was added propionyl chloride (0.6 mL) dropwise over one hour. The ice bath was removed after one hour, and the reaction stirred 24 hours at room temperature. Water (5 mL) was added and the bulk of pyridine was removed on the rotary evaporator at 2 Torr. The residue was dissolved in 1N HCL (5 mL) and the desired product extracted with CHCl$_3$ (2×20 mL). The combined organic extracts were dried (MgSO$_4$) and concentrated under vacuum. Purification of the crude product by flash column chromatography using silica gel afforded pentaerythritol dibutyrate dipropionate (0.6 g).

EXAMPLE 6

The process of Example 5 was repeated using a partially esterified pentaerythritol and the appropriate acid halide, imidazolide or anhydride. The following esters were prepared:

(a): pentaerythrityl monobutyratetripropionate
(b): pentaerythrityl dibutyratemonopropionate
(c): pentaerythrityl monobutyratedipropionate
(d): pentaerythrityl tributyratemonopropionate
(e): pentaerythrityl monobutyratetrihexanoate
(f): pentaerythrityl dibutyratemonohexanoate
(g): pentaerythrityl dibutyradihexanoate
(h): pentaerythrityl tributyratemonohexanoate

EXAMPLE 7

In this example, the compounds of Examples 1 and 2, i.e. tributyrin, dicaprylin, dicaproin, pentaerythrityl tributyrate, pentaerythrityl dihexanoate, and pentaerythrityl trihexanoate, were evaluated to determine the effectiveness of each ester in repelling potato aphids.

To do so, an artificial leaf was created for each ester according to the teaching of Ave et al. (Phenolic constituents of glandular trichomes on *Solanum berthaultii* and *S. polyadenium*, Amer. Potato J. 63: 473–480, 1986) by enclosing a 20% weight percent sucrose solution within Parafilm.

Two feeding ports were provided for each ester, each port having an area of 1 sq cm. To insure even coverage of the ester on the Parafilm, 2.5 ul of a solution of each noncyclic ester was dissolved in a mixture of acetone, chloroform, and paraffin oil (15:3:1) and was uniformly applied onto the feeding membrane surface.

Replicated tests of a choice assay (wherein one feeding port is covered with solvents only while the other includes the esters) showed a significant avoidance of the feeding area treated with the esters when potato aphids (*Macrosiphum euphorbiae*) were placed within the feeding chamber allowed to feed on the enclosed sucrose solution. There was a significant reduction in feeding when the ester mixture was used in the amount as low as 50 ug/cm. There was complete avoidance of the test port at a concentrations of 100 ug/cm and higher. Tributyrin, in particular, demonstrated excellent results.

Replicated tests of no-choice assay (wherein both feeding ports are covered and the ester mixture) demonstrated that between 50 to 100 ug/cm² of the ester was required to provide a deterrent response after about 1 hour.

Table I shows that these esters have a total number of 8, 10, 12 and 18 carbon atoms in their respective ester groups. Each of these esters has either 3 or 5 carbon atoms R, and 0, 1, 2 or 3 hydroxyl groups m. Each of these insect-repelling esters have 2 or 3 ester groups n, wherein each ester group has 4, 5, or 6 carbon atoms $R^1$.

TABLE I

| Ester | R | m | n | $R^1$ | Total ester C atoms |
|---|---|---|---|---|---|
| Tributyrin | 3 | 0 | 3 | 4 | 8 |
| Dicaprylin | 3 | 1 | 2 | 5 | 12 |
| Dicaproin | 3 | 1 | 2 |  | 10 |
| Pentaerythrityl tributyrate | 5 | 2 | 3 | 4 | 12 |
| Pentaerythrityl dihexanoate | 5 | 3 | 2 | 6 | 12 |

TABLE I-continued

| Ester | R | m | n | $R^1$ | Total ester C atoms |
|---|---|---|---|---|---|
| Pentaerythrityl trihexanoate | 5 | 1 | 3 | 6 | 18 |

COMPARATIVE EXAMPLE A

The procedure of Example 3 was repeated for the following esters which are outside the scope of the present invention:

(a): 1,3-di-n-decyl ester of glycerol
(b): pentabutylester of D-fructose
(c): pentaerythrityl monobutyrate
(d): pentaerythrytyl tetrahexanoate None of these esters was found to have any effect upon the feeding behavior of the aphids.

Table II shows that all of these ineffective insect-repelling esters have a total number of carbon atoms that is less than 9 and greater than 19 in their respective ester groups. The R groups in these esters have 3, 5, or 6 carbon atoms, and the esters have 0, and 3 hydroxyl groups m. These esters have 1, 2, 4, or 5 ester groups n, wherein each ester group has 4, 6 or 10 carbon atoms $R^1$.

TABLE II

| Ester | R | m | n | $R^1$ | Total Carbon atoms |
|---|---|---|---|---|---|
| 1,3-di-n-decyl ester of glycerol | 3 | 1 | 2 | 10 | 20 |
| Pentabutylester of D-fructose | 6 | 1 | 5 | 4 | 20 |
| Pentaerythrityl monobutyrate | 5 | 3 | 1 | 4 | 4 |
| Pentaerythrityl tetrahexanoate | 5 | 0 | 4 | 6 | 24 |

EXAMPLE 8

The procedures of Example 3 and Comparative Example A are repeated except that the aphids are replaced by each of the following insects:

(a): tarsonemid mites
(b): carmide spider mites
(c): two spotted spider mites
(d): leaf beetles
(e): tobacco flea beetles
(f): leafminer beetles
(g): aster leafhoppers
(h): citrus mealybigs
(i): silverleaf whiteflies
(j): potato tubermoths
(k): beet armyworms In each case, insect repellency is observed when one or more feeding ports are coated with a thin layer of the esters of the present invention, thought the amounts required for total avoidance varied. In each case, no insect repellency is observed when one or more feeding ports are coated with a thin layer of the esters of Comparative Example A.

What is claimed is:

1. A method for repelling an insect from a surface of a plant which comprises applying thereto an insect repellent amount of an ester of the formula:

$$(OH)_m-R-(O-CO-R^1)_n$$

wherein R is a non-cyclic straight or branched chain hydrocarbon group having from about 3 to about 5 carbon atoms; $R^1$ is an alkyl group having from about 1 to about 18 carbon atoms; m is an integer from about 0 to about 5; n is an integer of at least 2 and up to about 6; m+n is an integer of at least 3; and the total number of carbon atoms in the $R^1$ groups is about 9 to about 19.

2. The method of claim 1, wherein each $R^1$ is the same.

3. The method of claim 1, wherein at least two $R^1$ groups are different.

4. The method of claim 1, wherein the insect repellent ester is blended with an inert solid carrier.

5. The method of claim 1, wherein the insect repellent ester is blended with an inert liquid carrier.

6. The method of claim 1, wherein R is derived from glycerol.

7. The method of claim 1, wherein R is derived from pentaerythritol.

8. A method for deterring an insect from feeding or ovipositing on a plant which comprises treating the surfaces of the plant with a feeding deterrent amount of an ester of the formula:

$$(OH)_m-R-(O-CO-R^1)_n$$

wherein R is a non-cyclic straight or branched chain hydrocarbon group having from about 3 to about 5 carbon atoms; $R^1$ is an alkyl group having from about 1 to about 18 carbon atoms; m is an integer from about 0 to about 5; n is an integer of at least 2 and up to about 6; m+n is an integer of at least 3; and the total number of carbon atoms in the $R^1$ groups is about 9 to about 19.

9. The method of claim 8, wherein the insect is selected from the group consisting of tarsonemid mites, carmine spider mites, two spotted spider mites, leaf beetles, tobacco flea beetles, tomato flea beetles, flea beetles, tobacco flea beetles, leafminer flies, cowpea aphids, bean aphids, melon aphids, foxglove aphids, aphids, potato leafhoppers, potato aphids, aster leafhoppers, green peach aphids, citrus mealey bugs, silverleaf whitefly, and greenhouse whiteflies.

10. The method of claim 8, wherein the plant is selected from the group consisting of ornamental plants and productive plants.

11. The method of claim 9, wherein the ornamental plants are selected from the group consisting of roses, chrysanthemums, carnations, poinsettias, and impatiens.

12. The method of claim 9, wherein the productive plants are selected from the group consisting of corn, soybean, sunflower, tomato, tobacco, potato, wheat, oats, and alfalfa.

13. The method of claim 8, wherein the insect repellent ester is blended with an inert solid carrier.

14. The method of claim 8, wherein the insect repellent ester is blended with an inert liquid carrier.

15. The method of claim 8, wherein R is derived from glycerol.

16. The method of claim 8, wherein R is derived from pentaerythritol.

17. A composition which comprises an ester of the formula:

$$(OH)_m-R-(O-CO-R^1)_n$$

wherein R is a non-cyclic straight or branched chain hydrocarbon group having from about 3 to about 5 carbon atoms; $R^1$ is an alkyl group having from about 1 to about 18 carbon atoms; m is an integer from about 0 to about 5; n is an integer of at least 2 and up to about 6; m+n is an integer of at least 3; and the total number of carbon atoms in the $R^1$ groups is about 9 to about 19; in combination with an inert carrier on a plant surface for deterring an insect from feeding or ovipositing on the plant surface.

18. The composition of claim 17, wherein each $R^1$ is the same.

19. The composition of claim 17, wherein at least two $R^1$ groups are different.

20. The composition of claim 17, wherein the inert carrier is selected from the group consisting of liquid carriers and solid carriers.

21. The composition of claim 17, wherein R is derived from glycerol.

22. The composition of claim 17, wherein R is derived from pentaerythritol.

* * * * *